United States Patent
Lin et al.

(10) Patent No.: US 10,426,343 B2
(45) Date of Patent: Oct. 1, 2019

(54) PHYSIOLOGY DETECTING GARMENT, PHYSIOLOGY DETECTING MONITORING SYSTEM AND MANUFACTURING METHOD OF TEXTILE ANTENNA

(71) Applicant: INDUSTRIAL TECHNOLOGY RESEARCH INSTITUTE, Hsinchu (TW)

(72) Inventors: Hong-Dun Lin, Hsinchu (TW); Wen-Hsien Sun, Taoyuan (TW); Yong-Syuan Chen, Taichung (TW); Chih-Lung Chen, Hsinchu County (TW); Yen-Hsien Lee, Taipei (TW); Pei-Fen Zhen, Hsinchu County (TW); Jing-Wen Tang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 334 days.

(21) Appl. No.: 15/243,295

(22) Filed: Aug. 22, 2016

(65) Prior Publication Data
US 2017/0265743 A1   Sep. 21, 2017

Related U.S. Application Data

(60) Provisional application No. 62/309,474, filed on Mar. 17, 2016.

(51) Int. Cl.
*A61B 5/00* (2006.01)
*H01Q 1/27* (2006.01)
(Continued)

(52) U.S. Cl.
CPC ............ *A61B 5/002* (2013.01); *A61B 5/0006* (2013.01); *A61B 5/0205* (2013.01); *A61B 5/08* (2013.01);
(Continued)

(58) Field of Classification Search
CPC ..... A61B 5/0006; A61B 5/0015; A61B 5/002; A61B 5/0205; A61B 5/024; A61B 5/08;
(Continued)

(56) References Cited

U.S. PATENT DOCUMENTS

| 4,016,868 A | 4/1977 | Allison |
| 6,551,252 B2 | 4/2003 | Sackner et al. |

(Continued)

FOREIGN PATENT DOCUMENTS

| CN | 102727182 A | 10/2012 |
| CN | 204125790 U | 1/2015 |

(Continued)

OTHER PUBLICATIONS

Li, Zhuo, et al. "Highly Conductive, Flexible, Polyurethane-Based Adhesives for Flexible and Printed Electronics". Advanced Functional Materials. vol. 23 Issue 11. pp. 1459-1465. (Year: 2013).*

(Continued)

*Primary Examiner* — Michael J Carey
(74) *Attorney, Agent, or Firm* — Muncy, Geissler, Olds & Lowe, P.C.

(57) ABSTRACT

A physiology detecting garment, a physiology detecting monitoring system, and a manufacturing method of a textile antenna are provided. The physiology detecting garment detects and collects physiology information of a wearer. The physiology detecting garment includes a garment, a textile antenna and a detecting device. The textile antenna is made of a conductive composition including a conductive nanowire and a polyurethane polymer. The textile antenna is thermal-compression bonded to the garment. The detecting device is electrically connected to the textile antenna and emits a detecting signal via the textile antenna.

34 Claims, 5 Drawing Sheets

(51) Int. Cl.
*A61B 5/08* (2006.01)
*A61B 5/0205* (2006.01)
*A61B 5/11* (2006.01)
*A61B 5/024* (2006.01)
*H04W 4/80* (2018.01)

(52) U.S. Cl.
CPC .......... *A61B 5/1116* (2013.01); *A61B 5/6804* (2013.01); *A61B 5/7203* (2013.01); *H01Q 1/273* (2013.01); *A61B 5/0015* (2013.01); *A61B 5/024* (2013.01); *A61B 2560/0443* (2013.01); *A61B 2562/12* (2013.01); *H04W 4/80* (2018.02)

(58) Field of Classification Search
CPC ... A61B 5/1116; A61B 5/6804; A61B 5/7203; A61B 2560/0443; A61B 2562/12; H01Q 1/273; H04W 4/80
USPC .................................................. 600/300, 301
See application file for complete search history.

(56) References Cited

U.S. PATENT DOCUMENTS

| | | | |
|---|---|---|---|
| 7,670,295 | B2 | 3/2010 | Sackner et al. |
| 7,698,101 | B2 | 4/2010 | Alten et al. |
| 7,760,082 | B2 | 7/2010 | Wong et al. |
| 8,099,258 | B2 | 1/2012 | Alten et al. |
| 8,630,586 | B2 | 1/2014 | Dvortsov et al. |
| 8,762,733 | B2 | 6/2014 | Derchak et al. |
| 8,818,478 | B2 | 8/2014 | Scheffler et al. |
| 8,909,318 | B2 | 12/2014 | Nordstrom |
| 8,945,328 | B2 | 2/2015 | Longinotti-Buitoni et al. |
| 8,948,839 | B1 | 2/2015 | Longinotti-Buitoni et al. |
| 8,978,452 | B2 | 3/2015 | Johnson et al. |
| 2006/0258914 | A1 | 11/2006 | Derchak et al. |
| 2008/0221401 | A1 | 9/2008 | Derchak et al. |
| 2010/0274100 | A1 | 10/2010 | Behar et al. |
| 2010/0292568 | A1 | 11/2010 | Droitcour et al. |
| 2012/0184826 | A1 | 7/2012 | Keenan et al. |
| 2014/0318857 | A1 | 10/2014 | Sun et al. |
| 2015/0040282 | A1* | 2/2015 | Longinotti-Buitoni ..................... A61B 5/6804 2/69 |
| 2017/0172439 | A1* | 6/2017 | Zhu .......... B32B 15/06 |

FOREIGN PATENT DOCUMENTS

| | | |
|---|---|---|
| TW | I337786 | 2/2011 |
| TW | I480357 | 4/2015 |
| TW | M523718 | 6/2016 |
| WO | WO 2015/138515 A1 | 9/2015 |

OTHER PUBLICATIONS

Gregorio López, et al., "LOBIN: E-Textile and Wireless-Sensor-Network-Based Platform for Healthcare Monitoring in Future Hospital Environments", IEEE *Transactions on Information Technology in Biomedicine*, vol. 14, No. 6, Nov. 2010, pp. 1446-1458.

* cited by examiner

PHYSIOLOGY DETECTING GARMENT, PHYSIOLOGY DETECTING MONITORING SYSTEM AND MANUFACTURING METHOD OF TEXTILE ANTENNA

This application claims the benefit of U.S. provisional application Ser. No. 62/309,474, filed Mar. 17, 2016, the subject matter of which is incorporated herein by reference.

TECHNICAL FIELD

The present disclosure relates to a physiology detecting garment, a physiology detecting monitoring system and a manufacturing method of a textile antenna.

BACKGROUND

As modern people put more and more emphasis on life qualities along with the gradual aging of population, many domesticated simple medical devices and wearable physiology detecting devices are developed correspondingly. Such devices can be used for medical care and physiological monitoring of elderly people, and can be used as well for detecting physiology conditions of such as respiration, pulses, sport postures or caloric consumptions during exercise.

Therefore, how to simplify the manufacturing methods of conductive components in wearable detecting devices and how to manufacture physiology detecting garments which do not require contacting wearer's skins have been technical issues that the industry has been working on.

SUMMARY

According to an embodiment of the present disclosure, a physiology detecting garment is provided. The physiology detecting garment detects and collects a physiology information of a wearer. The physiology detecting garment includes a garment, a textile antenna and a detecting device. The textile antenna is made of a conductive composition, the conductive composition including a conductive nanowire and a polyurethane polymer, and the textile antenna is thermal-compression bonded to the garment. The detecting device is electrically connected to the textile antenna and emits a detecting signal via the textile antenna.

According to another embodiment of the present disclosure, a physiology detecting monitoring system is provided. The physiology detecting monitoring system detects and collects a physiology information of a wearer. The physiology detecting monitoring system includes a garment, a textile antenna, a detecting device and an electronic device. The textile antenna is made of a conductive composition, the conductive composition including a conductive nanowire and a polyurethane polymer, and the textile antenna is thermal-compression bonded to the garment. The detecting device is electrically connected to the textile antenna. The detecting device emits a first detecting signal and detects a second signal reflected from the wearer via the textile antenna. The electronic device is for analyzing the physiology information or the second detecting signal.

According to a further embodiment, a manufacturing method of a textile antenna is provided. The manufacturing method of the textile antenna includes the following steps: forming a conductive composition, the conductive composition including a conductive nanowire and a polyurethane polymer; performing a heating process to the conductive composition; and thermal-compression bonding the conductive composition to a garment according to a predetermined pattern for forming a textile antenna having the predetermined pattern, wherein the textile antenna is thermal-compression bonded to the garment.

The following description is made with reference to the accompanying drawings and embodiments.

DETAILED DESCRIPTION

In the embodiments of the present disclosure, the textile antenna made by mixing a conductive nanowire in a polyurethane polymer is thermal-compression bonded to the garment, such that the textile antenna is provided with improved adhesion, maintaining an excellent noise ratio, and having excellent fastness to washing. Details of embodiments of the present disclosure are described hereinafter with accompanying drawings. Specific structures and compositions disclosed in the embodiments are for examples and for explaining the disclosure only and are not to be construed as limitations. A person having ordinary skill in the art may modify or change corresponding structures and compositions of the embodiments according to actual applications.

Figure 1:
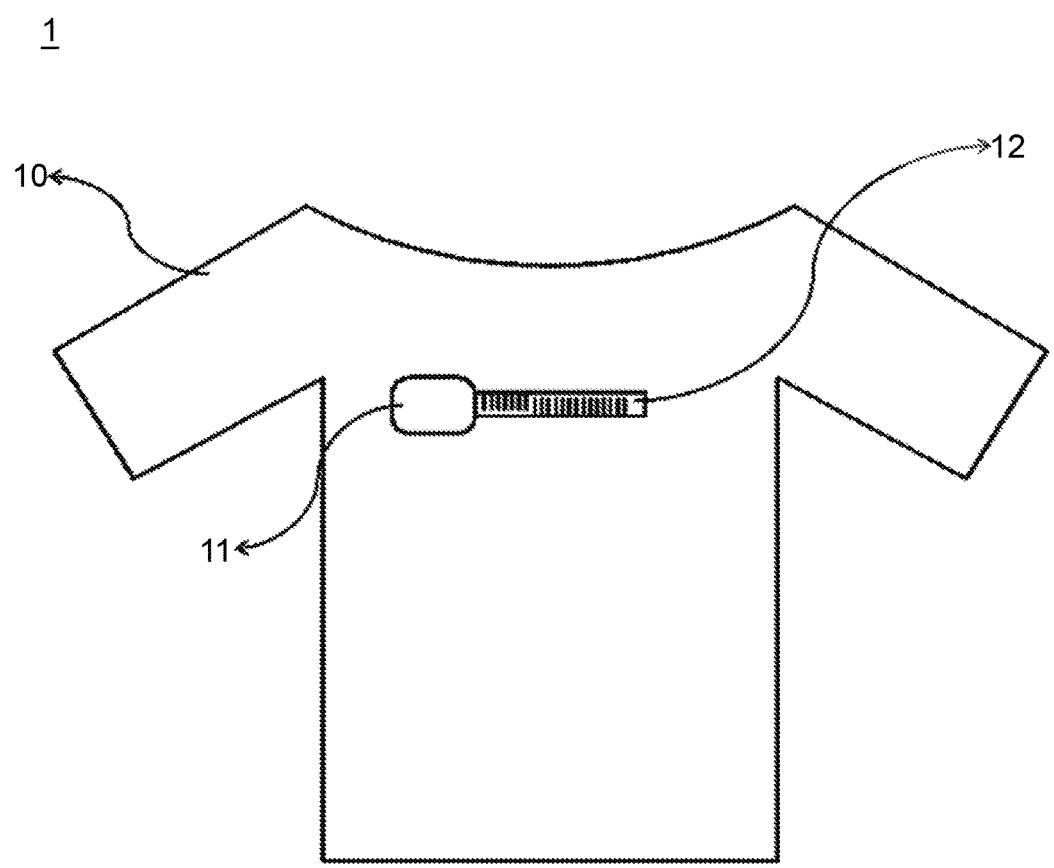
FIG. 1 shows a schematic drawing of a physiology detecting garment according to an embodiment of the present disclosure.

FIG. 1 shows a schematic drawing of a physiology detecting garment according to an embodiment of the present disclosure. As shown in FIG. 1, the physiology detecting garment 1 includes a garment 10, a textile antenna 12 and a detecting device 11. The textile antenna 12 is made of a conductive composition, the conductive composition includes a conductive nanowire and a polyurethane (PU), and the conductive composition may optionally further include a conductive adhesive. The textile antenna 12 is thermal-compression bonded to the garment 10. The detecting device 11 is electrically connected to the textile antenna 12 and emits a detecting signal via the textile antenna 12. According to the embodiments of the present disclosure, the physiology detecting garment 1 detects and collects a physiology information of a wearer wirelessly; that is, the physiology detecting garment 1 performs a non-contact type physiological detection. According to the embodiments of the present disclosure, the textile antenna 12 made by mixing the conductive nanowire in the polyurethane polymer is thermal-compression bonded to the garment 10, such that the textile antenna 12 can be provided with improved adhesion, maintaining an excellent noise ratio, and having excellent fastness to washing.

In the embodiment, the conductive nanowire is used as the conductive main body and mixed in the polyurethane polymer, and the tangled conductive wire(s) can provide improved adhesion. Moreover, the conductive nanowires, e.g. nano-silver wires, have superior expendability, thus the textile antenna 12 can be expended to a certain extent while still having excellent stability and further maintaining an excellent noise ratio.

The below table shows the results of tensile tests of the textile antenna according to an embodiment, showing resistance values and resistance variations before and after the tensile tests. In the below table, the conductive composition of the textile antenna of the embodiment includes 50 wt % of nano-silver wires, 45 wt % of a polyurethane polymer and 5 wt % of water, and the measured distances represent the distances between the multi-meter, the black probe and the red probe.

|  | Measured distance (cm) | | |
| --- | --- | --- | --- |
|  | 2 | 6 | 10 |
| Original resistance (Ω) | 0.63 | 0.67 | 0.73 |
| Resistance after the tensile test of a 2 Kg loading (Ω) | 0.63 | 0.69 | 0.77 |
| Resistance variation (%) | 0 | 2.99 | 5.48 |

As shown from the experimental results listed in the above table, even when the textile antenna is expanded to a certain extent, the textile antenna can still have excellent stability of resistance characteristics, and thus excellent noise ratios can be further provided. Moreover, the microscopic pictures (not shown) of the above textile antenna sample also show excellent surface morphology, indicating that excellent surface properties of the textile antenna can still be maintained even after expanded.

The garment 10 is such as a clothing, of which the material usually has holes. Normally, antenna patterns are formed on the clothing by coating a silver adhesive or silver particles on the clothing, in such case, the materials of the silver adhesive or the silver particle may crack due to the deformation of the clothing when expanded, and coating on the clothing surface with holes may cause bad adhesion. In addition, the manufacturing processes of evaporation deposition(s) or sputtering deposition(s) on the clothing followed by reduction reactions of nano-conductive particles are extremely complicated. On the contrary, according to the embodiments of the present disclosure, the textile antenna 12 is thermal-compression bonded to the garment 10, where the material of the textile antenna 12, e.g. the polyurethane polymer, and the material of the garment 10 undergo thermal-crosslink reactions, such that the manufacturing process is simple, and excellent adhesion can be provided between the textile antenna 12 and the garment 10.

In an embodiment, the conductive nanowire is covered by the polyurethane polymer, and thus the as-formed textile antenna 12 can have excellent washing fastness, and the textile antenna 12 can still have stable electrical properties after being washed by water.

Contact-type detecting devices and non-contact type detecting devices emit electromagnetic waves with different frequencies, patterns, and etc., and thus different design concerns of the materials and the shapes of the antennas are applied. According to the embodiments of the present disclosure, the textile antenna 12 made of the aforementioned conductive composition has excellent properties when used in non-contact type physiological detections.

As shown in FIG. 1, the garment 10 can be a short-sleeve shirt, and the textile antenna 12 is arranged on the chest portion and designed in form of a comb antenna. In the embodiment, the detecting device 11 is such as a low-power radar module. The detecting device 11 can emit a detecting signal onto the body of the wearer via the textile antenna 12, and the detecting device 11 receives the detecting signal reflected from the wearer to obtain a physiology information of the wearer, the physiology information including at least one of a pulse information, an electrocardiography information, a respiration information and a body posture information.

In the embodiment, the conductive nanowire is such as a nano-silver wire. The nano-silver wire is in an amount from such as 15 wt % to less than 60 wt % of the conductive composition. In some embodiments, the nano-silver wire is in an amount from such as 15 wt % to 45 wt % of the conductive composition.

In the embodiment, the textile antenna 12 is thermal-compression bonded to the garment 10 via the polyurethane polymer in the composition of the textile antenna 12. In the embodiment, the polyurethane polymer is such as a hydrophilic polyurethane polymer having one or more than one hydrophilic functional group(s), such that an improved adhesion can be provided with the material of the garment 10, e.g. fabrics materials. In the embodiment, the polyurethane polymer is in an amount from such as 30 wt % to 45 wt % of the conductive composition.

In some embodiments, the polyurethane polymer includes such as one or more than one ester repeating unit(s). As such, this polyester-type polyurethane polymer has higher viscosity and can provide better waterproof effects for the textile antenna 12.

In the embodiments of the present disclosure, the polyurethane polymer may be a polyester-type hydrophilic polyurethane polymer. For example, the polyester-type hydrophilic polyurethane polymer may have multiple ester repeating units and one or more than one hydrophilic functional group(s).

In an embodiment, the polyester-type polyurethane polymer can be represented by such as the following chemical formula I:

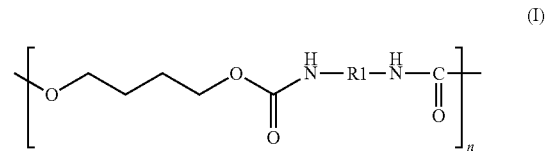

(I)

wherein n is an integer larger than 1, and R1 is

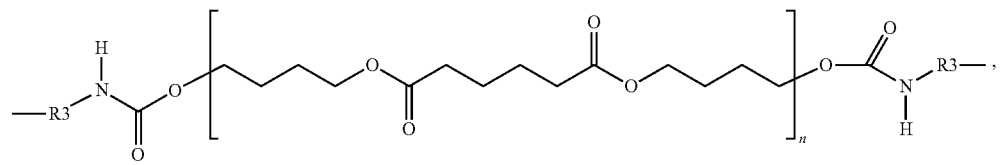

and
wherein R2 is

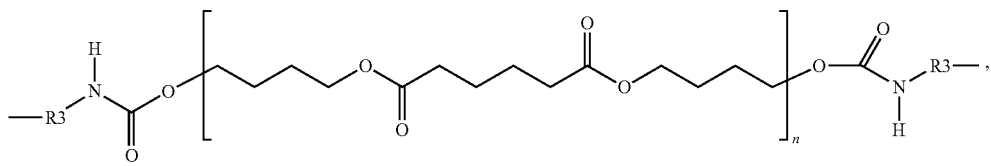

and
wherein R3 is

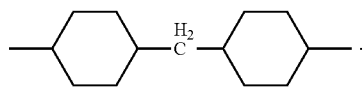

The polyester-type polyurethane polymer represented by the above chemical formula I has multiple ester repeating units and have hydrophilic carboxyl functional groups. The polyester-type polyurethane polymer represented by the above chemical formula I has a viscosity of about 35000 cps.

In some embodiments, the polyurethane polymer may be such as a polyether-type polyurethane polymer having one or more than one ether repeating unit(s).

In an embodiment, the polyether-type polyurethane polymer can be represented by such as the following chemical formula II:

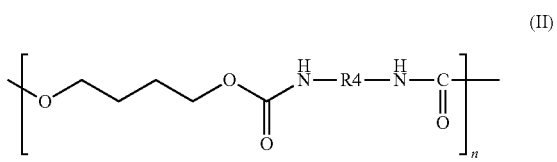

(II)

wherein n is an integer larger than 1, and R4 is

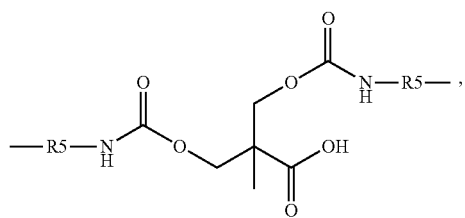

where R5 is

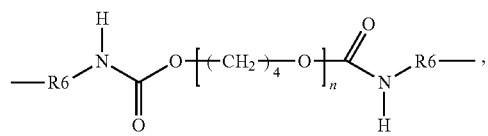

and
wherein R6 is

The polyether-type polyurethane polymer represented by the above chemical formula II has multiple ether repeating units and hydrophilic carboxyl functional groups. The polyether-type polyurethane polymer represented by the above chemical formula II has a viscosity of about 15000 cps.

According to the embodiments of the present disclosure, the textile antenna 12 that is resistant to water-washing and can be nicely adhered to the garment 10 can be manufactured by applying the above-mentioned conductive composition.

According to the embodiments of the present disclosure, a manufacturing method of a textile antenna 12 is provided. The manufacturing method includes such as the following steps.

First, a conductive composition is formed. The steps of forming the conductive composition may include mixing a conductive nanowire and a polyurethane polymer. In some embodiments, a conductive adhesive can be further optionally mixed therein. In the conductive composition, the conductive nanowire is in an amount from such as 15 wt % to 45 wt % of the conductive composition, the polyurethane polymer is in an amount from such as 35 wt % to 45 wt % of the conductive composition, and the remaining may be water.

The conductive adhesive used in some of the embodiments of the present disclosure is chosen from the conductive adhesive disclosed in Taiwan patent No. I480357, of which the composition includes 100 weight parts of copper powders, 40 to 150 weight parts of silver powders, 0.1 to 3 weight parts of carbon powers with a specific surface area of $200 \, m^2/g$ to $1000 \, m^2/g$, 1 to 5 weight parts of glass powders, and 5 to 15 weight parts of a binding agent. However, the above-described conductive adhesive is for examples and for explaining the disclosure only and are not to be construed as limitations. A person having ordinary skill in the art may modify or change the composition of the conductive adhesive according to actual applications.

Next, a heating process is performed to the conductive composition. In the embodiment, the heating process may be performed at such as 130-160° C. Moreover, the conductive composition is thermal-compression bonded to a garment 10 according to a predetermined pattern for forming a textile antenna 12 having the predetermined pattern, and the as-formed textile antenna 12 is thermal-compression bonded to the garment 10.

Since the textile antenna 12 is made of the conductive composition, the material of the garment 10 and the polyurethane polymer in the conductive composition undergo thermal-crosslink reactions, such that the textile antenna 12 is thermal-compression bonded to the garment 10 via the polyurethane polymer.

Figure 2:
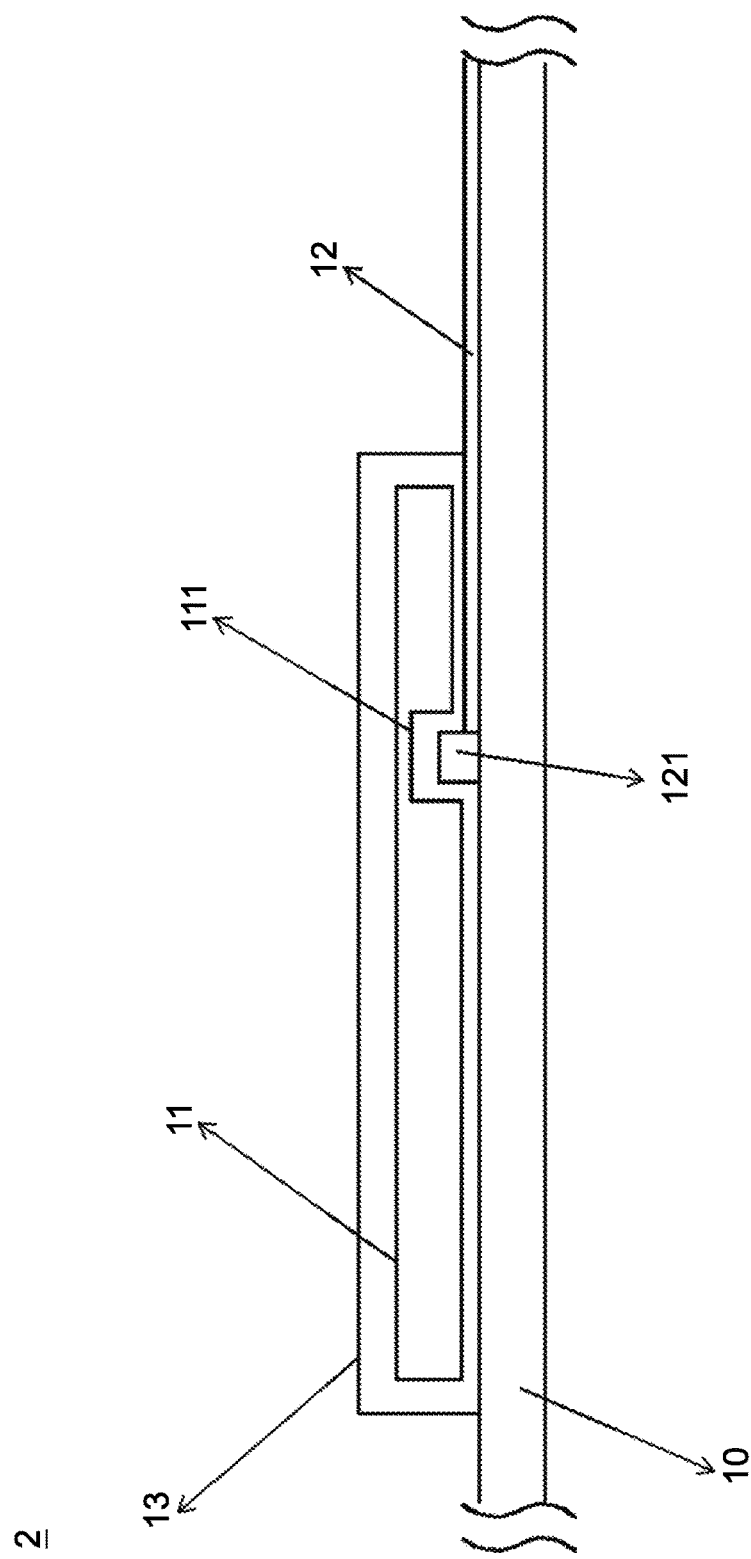
FIG. 2 shows a schematic drawing of a detecting device electrically connected to a textile antenna according to an embodiment of the present disclosure.

FIG. 2 shows a schematic drawing of a detecting device electrically connected to a textile antenna according to an embodiment of the present disclosure. The elements in the present embodiment sharing the same or similar labels with those in the previous embodiment are the same or similar elements, and the description of which is omitted.

In the embodiment, as shown in FIG. 2, the textile antenna 12 includes at least one conductive terminal 121, the detecting device 11 includes at least one contact 111, and the textile antenna 12 is electrically connected to the at least one contact 111 via the at least one conductive terminal 121.

In the embodiment, as shown in FIG. 2, the physiology detecting garment 2 may further include a waterproof material 13, the detecting device 11 is disposed on the garment 10, and the waterproof material 13 covers the detecting device 11. Due to that the detecting device 11 is sealed and fixed on the surface of the garment 10 by the waterproof material 13, with this type of waterproof design, a user can wash and clean the garment 10 without influencing the functions of the detecting device 11.

Figure 3:
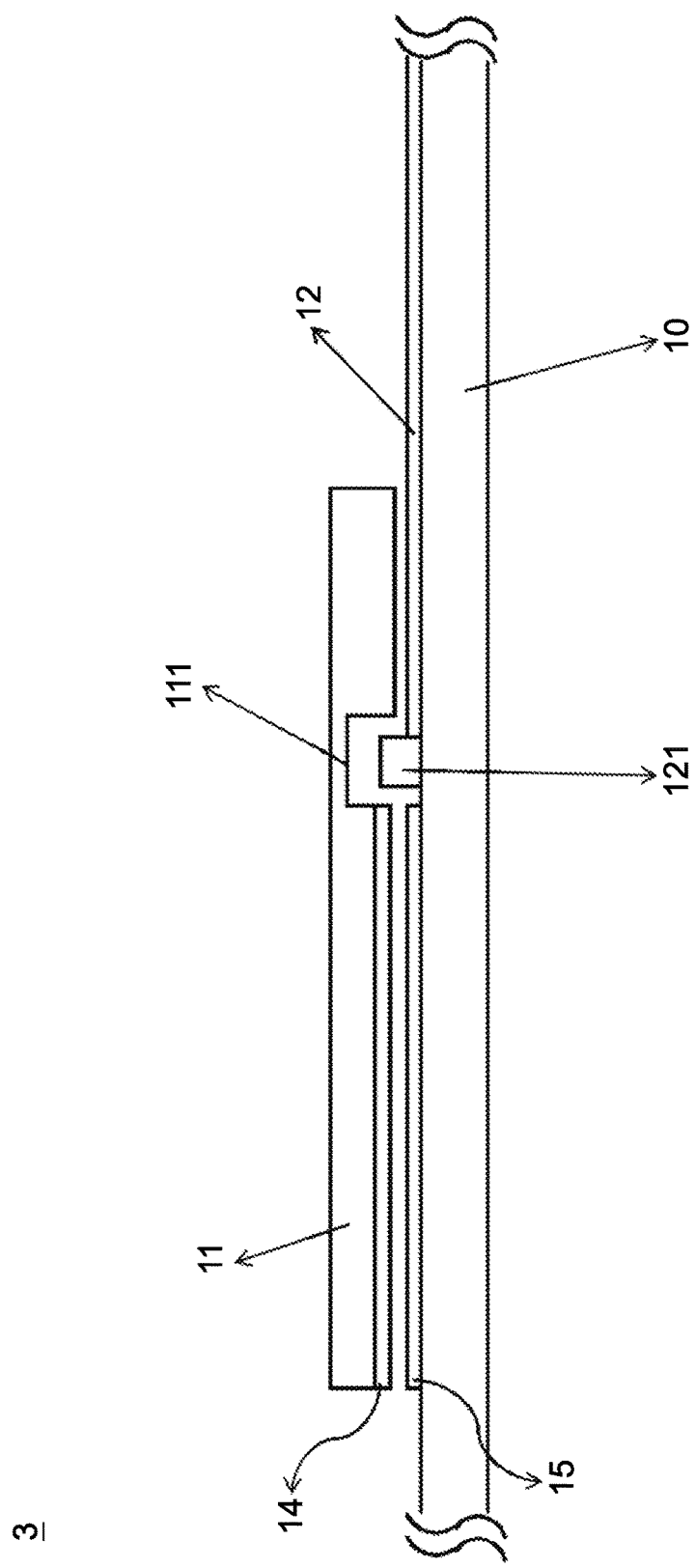
FIG. 3 shows a schematic drawing of a detecting device electrically connected to a textile antenna according to another embodiment of the present disclosure.

FIG. 3 shows a schematic drawing of a detecting device electrically connected to a textile antenna according to another embodiment of the present disclosure. The elements in the present embodiment sharing the same or similar labels with those in the previous embodiments are the same or similar elements, and the description of which is omitted.

In the embodiment, as shown in FIG. 3, the detecting device 11 of the physiology detecting garment 3 may be fixed to the garment 10 via a detachable buckling way.

For example, as shown in FIG. 3, the physiology detecting garment 3 may further include Nylon buckles 14 and 15, which are so-called Velcro. The surface of the garment 10 is disposed with the Nylon buckle 15, and the bottom surface of the detecting device 11, which is where the garment 10 is adhered, is disposed with another Nylon buckle 14. As such, the detecting device 11 can be adhered to the garment 10 via the Nylon buckles 14 and 15. When a user wants to wash and clean the garment 10 or needs to change a different type of a detecting device 11, the detecting device 11 can be easily detached from the garment 10.

Figure 4:
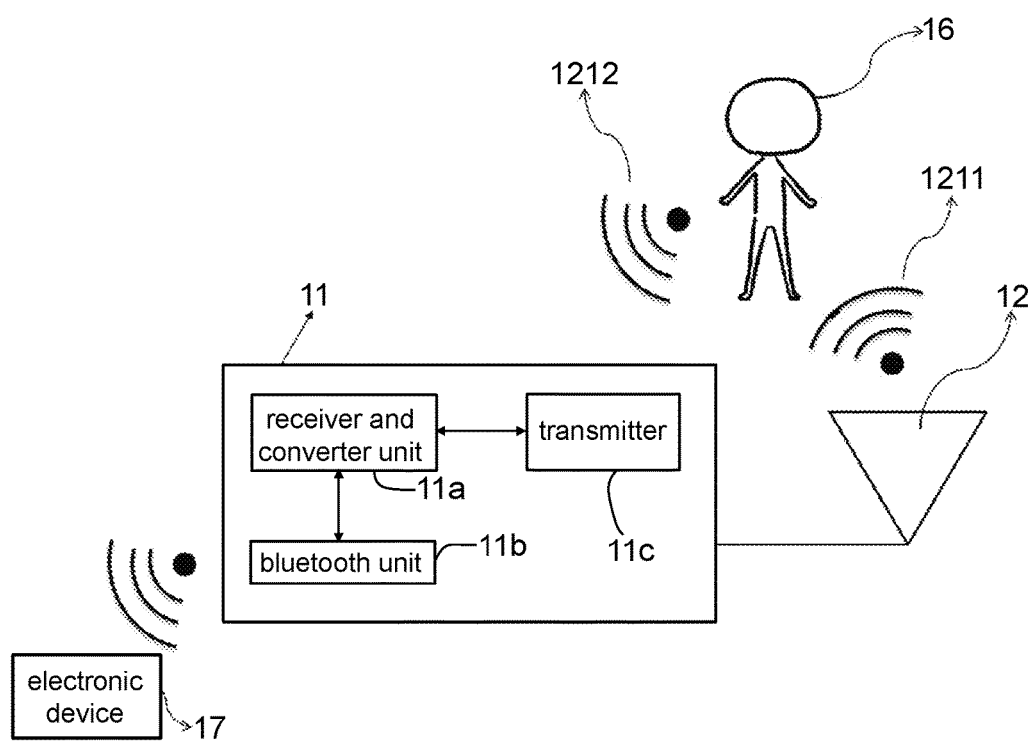
FIG. 4 shows a schematic drawing of a physiology detecting monitoring system according to an embodiment of the present disclosure.

FIG. 4 shows a schematic drawing of a physiology detecting monitoring system according to an embodiment of the present disclosure. The elements in the present embodiment sharing the same or similar labels with those in the previous embodiments are the same or similar elements, and the description of which is omitted.

As shown in FIG. 4, the physiology detecting monitoring system 4 includes an aforementioned garment (not shown in the current drawing), a textile antenna 12, a detecting device 11, and an electronic device 17. The textile antenna 12 is made of an aforementioned conductive composition, and the textile antenna 12 is thermal-compression bonded to the garment. The detecting device 11 is electrically connected to the textile antenna 12, and the detecting device 11 emits a first detecting signal 1211 and detects a second detecting signal 1212 reflected from the wearer 16 via the textile antenna 12. The electronic device 17 is for analyzing the physiology information or the second detecting signal 1212.

In the embodiment, the detecting device 11 can convert the second detecting signal 1212 to the physiology information and transmits the physiology information to the electronic device 17 wirelessly.

For example, as shown in FIG. 4, the detecting device 11 is such as a low-power radar module and includes a receiver and converter unit 11a, a bluetooth unit 11b, and a transmitter 11c. The transmitter 11c of the detecting device 11 emits a first detecting signal 1211 of such as 300 MHz to the wearer 16 via the textile antenna 12, and the receiver and converter unit 11a of the detecting device 11 receives the second detecting signal 1212 reflected from the wearer 16 and converts the second detecting signal 1212 to the physiology information of the wearer 16, the physiology information including a pulse information, an electrocardiography information, a respiration information, a body posture information, and etc. Then, the physiology information can be transmitted to the electronic device 17 via the bluetooth unit 11b wirelessly for analysis or representation.

In the embodiment, the electronic device 17 may include a portable electronic device or a stationary electronic device. For example, the electronic device 17 may be a portable electronic device such as a laptop computer, a tablet, a personal digital assistant, a mobile phone, a watch, or a game machine and etc., or the electronic device 17 may be a stationary electronic device such as a desktop computer. The electronic device 17 can be connected not only wirelessly to the detecting device 11 for transmitting information, but the electronic device 17 can also be wire connected to or directly installed on the detecting device 11 for transmitting information to the detecting device 11.

Figure 5:
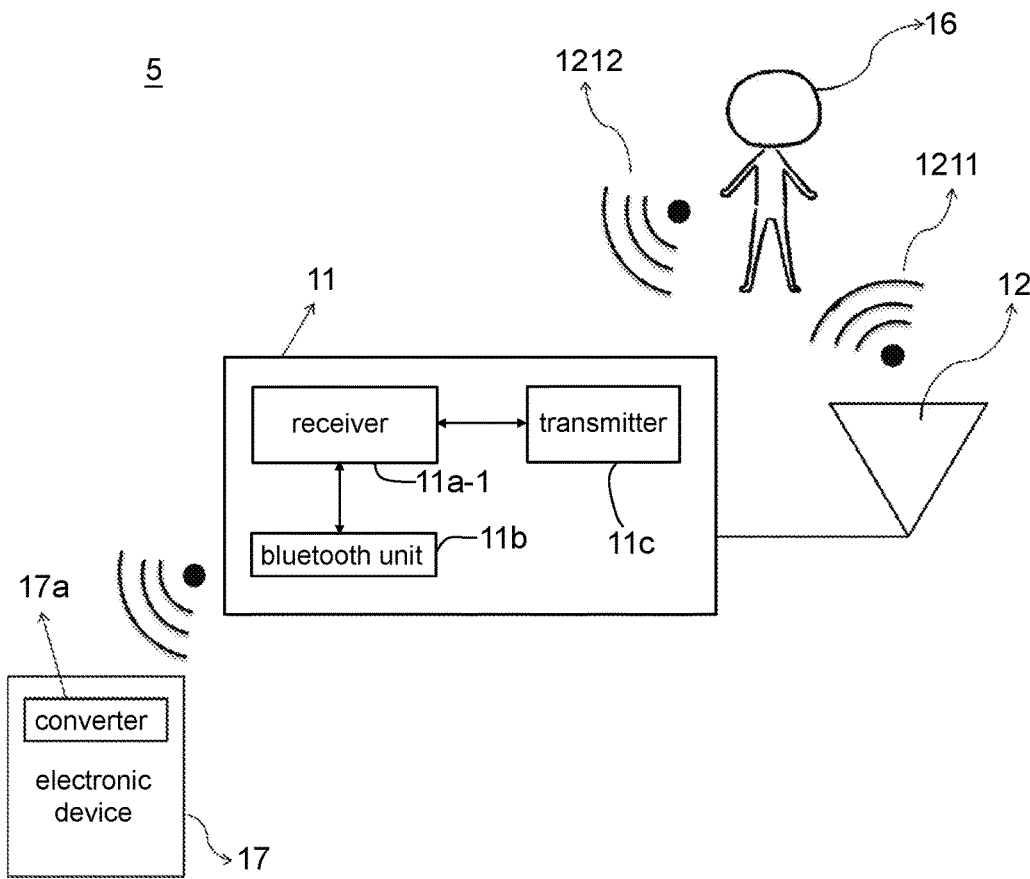
FIG. 5 shows a schematic drawing of a physiology detecting monitoring system according to another embodiment of the present disclosure.

FIG. 5 shows a schematic drawing of a physiology detecting monitoring system according to another embodiment of the present disclosure. The elements in the present embodiment sharing the same or similar labels with those in the previous embodiments are the same or similar elements, and the description of which is omitted.

The present embodiment is mainly different from the embodiment described in FIG. 4 in that, in the present embodiment, the detecting device 11 of the physiology detecting monitoring system 5 transmits the second detecting signal 1212 to the electronic device 17 wirelessly, and the second detecting signal 1212 is converted to the physiology information via the electronic device 17.

For example, as shown in FIG. 5, the detecting device 11 is arranged with only one receiver 11a-1. After the receiver 11a-1 receives the second detecting signal 1212 reflected from the wearer 16, the detecting device 11 does not perform any signal conversion, the detecting device 11 transmits the second detecting signal 1212 directly to the electronic device 17 via the bluetooth unit 11b, and the second detecting signal 1212 is converted to the physiology information via the converter 17b arranged in the electronic device 17 for analysis or representation.

Further explanation is provided with the following embodiments. A conductive composition and the test results of properties of the textile antenna made of the conductive composition of the embodiment are listed, and several compositions and the conductive textiles made thereof of several comparative embodiments are listed, for showing the properties of the textile antenna made according to the embodiments of the disclosure. However, the following examples are for purposes of describing particular embodiments only, and are not intended to be limiting.

Table 1 shows the surface resistance variations of the textile antennas of the embodiments and the commercial available conductive textiles of comparative embodiments after water-wash tests. In table 1, the conductive composition of the textile antenna of the embodiment includes 50% of nano-silver wires, 45% of a polyurethane polymer and 5% of water. The comparative embodiments are a conductive textile made of commercial available electroplating silver fabrics, a conductive textile made from A company, a conductive textile made from X company, and a conductive textile made from L company. The conductive textiles made from A company, X company and L company all include 81% of conductive yarns and 9% of Lycra.

TABLE 1

| Water-wash tests | Conductive textile made of commercial available electroplating silver fabrics | A company | X company | L company | Textile antenna of the embodiment of the present disclosure |
|---|---|---|---|---|---|
| Before washed by water | 0.1 Ω/□ | 0.17 Ω/□ | 0.32 Ω/□ | 0.16 Ω/□ | 0.41 Ω/□ |
| After washed by water for 20 times | 100 Ω/□ | 100.45 Ω/□ | 228.86 Ω/□ | 22.94 Ω/□ | 0.81 Ω/□ |
| Variation (*100%) | 1000 | 590 | 714 | 142 | 1.98 |

According to the results in table 1, after washed by water for 20 times, the conductive textile made of commercial available electroplating silver fabrics and the conductive textiles made from other companies suffer from huge changes in surface resistance values. On the contrary, after washed by water for 20 times, the textile antenna of the embodiment of the present disclosure only increases from 0.41Ω/□ to 0.81Ω/□ with a variation of 1.98 times, showing that the textile antenna of the embodiment of the present disclosure can maintain stable electronic properties even after washed by water. According to the results in table 1, the textile antenna of the embodiment of the present disclosure satisfy level 4-5 of the regulations standards of washing fastness test (AATCC-61-2A) and perspiration resistance test (AATCC15-2009) provided by American Association of Textile Chemists and Colorist (AATCC).

Table 2 shows the results of tensile tests of the textile antenna of the embodiment in table 1. The changes of resistance values and noise ratios after tensile tests are listed.

TABLE 2

| | Expanding ratio (%) | | | | |
|---|---|---|---|---|---|
| | 0 | 6.25 | 12.5 | 31.25 | 50 |
| Resistance value | 8 Ω | 9 Ω | 9 Ω | 18 Ω | 55 Ω |
| Noise ratio | 24 dB | 24 dB | 22.5 dB | 21.5 dB | 20.5 dB |

According to the results in table 2, when the textile antenna of the embodiment of the present disclosure is expanded by 31.25%, the resistance value only increases by 10Ω; when the textile antenna of the embodiment of the present disclosure is expanded by 50%, the resistance value only increases by 47Ω; the noise ratios are constantly kept within the range of larger than 20 dB, which is benefited to the signal interpretation. The above results show that the textile antenna of the embodiment of the present disclosure can suffer from dramatic expanding extents, and such property allows this type of textile antenna to be widely applied in different types of textiles.

Table 3 shows the conductive compositions of embodiments and a composition of a comparative embodiment and the surface resistance values and signal-to-noise ratios (SNR) of the textile antennas made thereof. The ratios are represented in weight percentage (wt %) of each component in the overall conductive composition.

TABLE 3

| | Nano-silver wire | Polyurethane polymer | Water | Surface resistance value (Ω/□) | SNR |
|---|---|---|---|---|---|
| Embodiment 1-1 | 15% | 85% | 0% | $1.57*10^1$ | 7 |
| Embodiment 2-1 | 30% | 65% | 5% | $7.62*10^0$ | 12 |
| Embodiment 3-1 | 45% | 45% | 10% | $2.69*10^0$ | 20 |
| Comparative embodiment 1 | 60% | 30% | 10% | $8.09*10^{-1}$ | N/A |

According to the results in table 3, while the weight percentage of nano-silver wires is within 15-45%, the signal-to-noise ratios (SNR) can all reach 7 dB or higher, and especially when the weight percentage of nano-silver wires is 45%, the SNR can be 20 dB with a very low surface resistance value. However, when the weight percentage of nano-silver wires is 60%, despite having the lowest surface resistance value, the viscosity of the conductive composition with this weight percentage is too high, causing an ununiformed textile antenna pattern when the pattern of the textile antenna is thermal-compression bonded to the garment and thus unable to provide excellent antenna functions.

Table 4 shows the conductive compositions of embodiments and compositions of comparative embodiments and the surface resistance values of the textile antennas made thereof before and after washed by water. The ratios are represented in weight percentage (wt %) of each component in the overall conductive composition. PU-1 is the aforementioned polyester-type polyurethane polymer represented by chemical formula I, PU-2 is the aforementioned polyether-type polyurethane polymer represented by chemical formula II, Epoxy represents an epoxide resin, and PET represents polyethylene terephthalate.

TABLE 4

| | Nano-silver wire | Polymer | Water | Surface resistance value before water-wash (Ω/□) | Surface resistance value after water-wash (Ω/□) |
|---|---|---|---|---|---|
| Comparative embodiment 2-1 | 45% | PMMA (45%) | 10% | $3.60*10^0$ | Not conductive |
| Comparative embodiment 2-2 | 45% | Epoxy (45%) | 10% | $2.44*10^1$ | Not conductive |
| Comparative embodiment 2-3 | 45% | PET (45%) | 10% | $1.19*10^0$ | Not conductive |
| Embodiment 2-1 | 45% | PU-1 (45%) | 10% | $2.69*10^0$ | $5.61*10^0$ |
| Embodiment 2-2 | 45% | PU-2 (45%) | 10% | $2.47*10^0$ | $3.34*10^1$ |

According to the results in table 4, the textile antennas made of polyurethane polymers all have excellent washing fastness properties, wherein the textile antennas made of polyester-type polyurethane polymer have higher washing fastness properties than those made of polyether-type polyurethane polymer.

While the disclosure has been described by way of example and in terms of the exemplary embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A physiology detecting garment for detecting and collecting a physiology information of a wearer, the physiology detecting garment comprising:
    a garment;
    a textile antenna made of a conductive composition, the conductive composition comprising a conductive nanowire and a polyurethane polymer, wherein the textile antenna is thermal-compression bonded to the garment; and
    a detecting device electrically connected to the textile antenna and emitting a detecting signal via the textile antenna.

2. The physiology detecting garment according to claim 1, wherein the physiology detecting garment detects and collects the physiology information wirelessly.

3. The physiology detecting garment according to claim 1, wherein the textile antenna is thermal-compression bonded to the garment via the polyurethane polymer.

4. The physiology detecting garment according to claim 1, wherein the conductive nanowire is a nano-silver wire.

5. The physiology detecting garment according to claim 4, wherein the nano-silver wire is in an amount from 15 wt % to 45 wt % of the conductive composition.

6. The physiology detecting garment according to claim 1, wherein the polyurethane polymer has one or more than one ester repeating unit.

7. The physiology detecting garment according to claim 1, wherein the polyurethane polymer is in an amount from 30 wt % to 45 wt % of the conductive composition.

8. The physiology detecting garment according to claim 1, wherein the textile antenna comprises at least one conductive terminal, the detecting device comprises at least one contact, and the textile antenna is electrically connected to the at least one contact via the at least one conductive terminal.

9. The physiology detecting garment according to claim 1, further comprising a waterproof material, wherein the detecting device is disposed on the garment, and the waterproof material covers the detecting device.

10. The physiology detecting garment according to claim 1, wherein the detecting device is fixed to the garment via a detachable buckling way.

11. The physiology detecting garment according to claim 1, wherein the detecting device is a low-power radar module.

12. The physiology detecting garment according to claim 1, wherein the physiology information comprises at least one of a pulse information, an electrocardiography information, a respiration information and a body posture information.

13. A physiology detecting monitoring system for detecting and collecting a physiology information of a wearer, the physiology detecting monitoring system comprising:
    a garment;
    a textile antenna made of a conductive composition, the conductive composition comprising a conductive nanowire and a polyurethane polymer, wherein the textile antenna is thermal-compression bonded to the garment;
    a detecting device electrically connected to the textile antenna, the detecting device emitting a first detecting signal and detecting a second detecting signal reflected from the wearer via the textile antenna; and
    an electronic device for analyzing the physiology information or the second detecting signal.

14. The physiology detecting monitoring system according to claim 13, wherein the physiology detecting monitoring system detects and collects the physiology information wirelessly.

15. The physiology detecting monitoring system according to claim 13, wherein the textile antenna is thermal-compression bonded to the garment via the polyurethane polymer.

16. The physiology detecting monitoring system according to claim 13, wherein the conductive nanowire is a nano-silver wire.

17. The physiology detecting monitoring system according to claim 13, wherein the nano-silver wire is in an amount from 15 wt % to 45 wt % of the conductive composition.

18. The physiology detecting monitoring system according to claim 13, wherein the polyurethane polymer has one or more than one ester repeating unit.

19. The physiology detecting monitoring system according to claim 13, wherein the textile antenna comprises at least one conductive terminal, the detecting device comprises at least one contact, and the textile antenna is electrically connected to the at least one contact via the at least one conductive terminal.

20. The physiology detecting monitoring system according to claim 13, wherein the detecting device converts the second detecting signal to the physiology information and transmits the physiology information to the electronic device wirelessly.

21. The physiology detecting monitoring system according to claim 13, wherein the detecting device transmits the second detecting signal to the electronic device wirelessly and converts the second detecting signal to the physiology information.

22. The physiology detecting monitoring system according to claim 13, further comprising a waterproof material, wherein the detecting device is disposed on the garment, and the waterproof material covers the detecting device.

23. The physiology detecting monitoring system according to claim 13, wherein the detecting device is fixed to the garment via a detachable buckling way.

24. The physiology detecting monitoring system according to claim 13, wherein the detecting device is a low-power radar module.

25. The physiology detecting monitoring system according to claim 13, wherein the electronic device comprises a portable electronic device or a stationary electronic device.

26. The physiology detecting monitoring system according to claim 13, wherein the physiology information comprises at least one of a pulse information, an electrocardiography information, a respiration information and a body posture information.

27. A manufacturing method of a textile antenna, comprising:
- forming a conductive composition, the conductive composition comprising a conductive nanowire and a polyurethane polymer;
- performing a heating process to the conductive composition; and
- thermal-compression bonding the conductive composition to a garment according to a predetermined pattern for forming a textile antenna having the predetermined pattern, wherein the textile antenna is thermal-compression bonded to the garment.

28. The manufacturing method of the textile antenna according to claim 27, wherein the heating process is performed at 130-160° C.

29. The manufacturing method of the textile antenna according to claim 27, wherein the textile antenna is thermal-compression bonded to the garment via the polyurethane polymer.

30. The manufacturing method of the textile antenna according to claim 27, wherein the conductive nanowire is a nano-silver wire.

31. The manufacturing method of the textile antenna according to claim 30, wherein the nano-silver wire is in an amount from 15 wt % to 45 wt % of the conductive composition.

32. The manufacturing method of the textile antenna according to claim 27, wherein the polyurethane polymer is in an amount from 30 wt % to 45 wt % of the conductive composition.

33. The manufacturing method of the textile antenna according to claim 27, wherein the polyurethane polymer has one or more than one ester repeating unit.

34. The manufacturing method of the textile antenna according to claim 27, wherein the polyurethane polymer has one or more than one hydrophilic functional group.

* * * * *